(12) United States Patent
Zhao et al.

(10) Patent No.: US 8,697,048 B2
(45) Date of Patent: Apr. 15, 2014

(54) PEPTIDE AMPHIPHILE SUSPENSION TO PREVENT OR REDUCE TUMOR FORMATION FROM ADMINISTERED EMBRYONIC STEM CELLS

(75) Inventors: Li-Ru Zhao, Shreveport, LA (US); John A. Kessler, Chicago, IL (US)

(73) Assignee: Northwestern University, Evanston, IL (US)

( * ) Notice: Subject to any disclaimer, the term of this patent is extended or adjusted under 35 U.S.C. 154(b) by 245 days.

(21) Appl. No.: 13/333,348

(22) Filed: Dec. 21, 2011

(65) Prior Publication Data

US 2012/0093784 A1 Apr. 19, 2012

Related U.S. Application Data

(63) Continuation of application No. 11/018,622, filed on Dec. 21, 2004, now abandoned.

(60) Provisional application No. 60/532,249, filed on Dec. 23, 2003.

(51) Int. Cl.
*A61K 38/00* (2006.01)
*A61K 47/48* (2006.01)

(52) U.S. Cl.
USPC ............................ 424/93.1; 514/3.2; 514/9.3

(58) Field of Classification Search
None
See application file for complete search history.

(56) References Cited

U.S. PATENT DOCUMENTS

| | | | |
|---|---|---|---|
| 5,843,780 A | 12/1998 | Thomson | |
| 6,562,619 B1 | 5/2003 | Gearhart et al. | |

FOREIGN PATENT DOCUMENTS

| | | |
|---|---|---|
| WO | WO 00/52145 | 9/2000 |
| WO | WO 01/00650 | 1/2001 |
| WO | WO 03/070749 | 8/2003 |
| WO | WO 03/084980 | 10/2003 |

OTHER PUBLICATIONS

Silva et al. Selective Differentiation of Neural Progenitor Cells by High—Epitope Density Nanofibers. Science, 2004, vol. 303, pp. 1352-1361.*
Herberts et al. Risk factors in the development of stem cell therapy. Journal of Translational Medicine, 2011, vol. 9, pp. 1-14.*
Bhardwaj et al., "Sonic hedgehog induces the proliferation of primitive human hematopoietic cells via BMP regulation," Nature Immunology, 2001, 2:172-180.
Brustle et al, "In vitro-generated neural precursors participate in mammalian brain development," PNAS, 1997, 94(26):14809-14814.
Gourlet et al., "Interaction of lipophilic VIP derivatives with recombinant VIP1/PACAP and VIP2/PACAP receptors," Eur J Pharmacol, 1998, 354(1):105-111.
Grabel et al.,"Using EC and ES cell culture to study early development: recent observations on Indian hedgehog and Bmps," Int J Dev Biol., 1998, 42(7)917-925.
Hartgerink et al., "Peptide-amphiphile nanofibers: a versatile scaffold for the preparation of self-assembling materials," PNAS, 2002, 99:5133-5138.
Jackson et al., "Regeneration of ischemic cardiac muscle and vascular endothelium by adult stem cells," J Clin Invest, 2001, 107(11):1395-1402.
Langer & Ugorski, "The Macromolecular Aggregate as a Drug Carrier," Cellular and Molecular Biology Letters, 2000 5(4):433-440.
Lee et al., "Efficient generation of midbrain and hindbrain neurons from mouse embryonic stem cells," Nat Biotechnol, 2000, 18(6):675-679.
Matthew et al., "Effect of mammalian cell culture medium on the gelation properties of Pluronic F127," Biomaterials, 2002, 23(23):4615-4619.
Moody et al., "(Stearyl, Norleucine17)VIP hybrid antagonizes VIP receptors on non-small cell lung cancer cells," Life Sci., 1997, 61(17):1657-1666.
Nagarajan et al., "Aggregation of amphiphiles as micelles or vesicles in aqueous media," Journal of Colloid and Interface Science, 1979, 71(3):580-604.
O'Shea, "Directed differentiation of embryonic stem cells: genetic and epigenetic methods," Wound Repair Regen, 2001, 9(6):443-459.
Odorico et al., "Multilineage differentiation from human embryonic stem cell lines," Stem Cells, 2001, 19(3):193-204.
Ostenfeld et al., "Regional specification of rodent and human neurospheres," Brain Res Dev Brain Res, 2002, 134 (1-2):43-55.
Outram et al., "Hedgehog signaling regulates differentiation from double-negative to double-positive thymocyte," Immunity, 2000, 13(2):187-197.
Pakalns et al., "Cellular recognition of synthetic peptide amphiphiles in self-assembled monolayer films," Biomaterials, 1999, 20:2265-2279.
Platt, "New Directions for Organ Transplantation," 1998, 392 (SUPPL):11-17.
Rothstein & Snyder, "Reality and immortality—neural stem cells for therapies," Nat Biotechnol, 2004, 22(3):283-285.
Sigma-Aldrich catalog printout; Sigma-Aldrich catalog [online], 2009 [retrived Feb. 26, 2009] from http://www.sigmaaldrich.com/catalog/ProductDetail.do?N4=C8667|SIGMA&N5=SEARCH_CONTACT_PNO|BRAND_KEY&F=SPEC>, pp. 1-2.
Tashiro et al., "A synthetic peptide containing the IKVAV sequence from the A chain of laminin mediates cell attachment, migration, and neurite outgrowth," J Biol Chem, 1989, 264(27))16174-16182.
Toda et al., "Grafting neural stem cells improved the impaired spatial recognition in ischemic rats," Neurosci Lett., 2001, 316(1):9-12.
Yu et al., "Minimal Lipidation Stabilizes Protein-Like Molecular Architecture," J Am Chem Soc, 1998, 120(39):9979-9987.

* cited by examiner

*Primary Examiner* — Deborah Crouch
(74) *Attorney, Agent, or Firm* — Casimir Jones, S.C.

(57) ABSTRACT

The present invention relates to the use of self-assembling peptide amphiphiles to prevent tumor formation by transplanted stem cells. The present invention further relates to the use of self-assembling peptide amphiphiles to treat cancers.

3 Claims, 1 Drawing Sheet

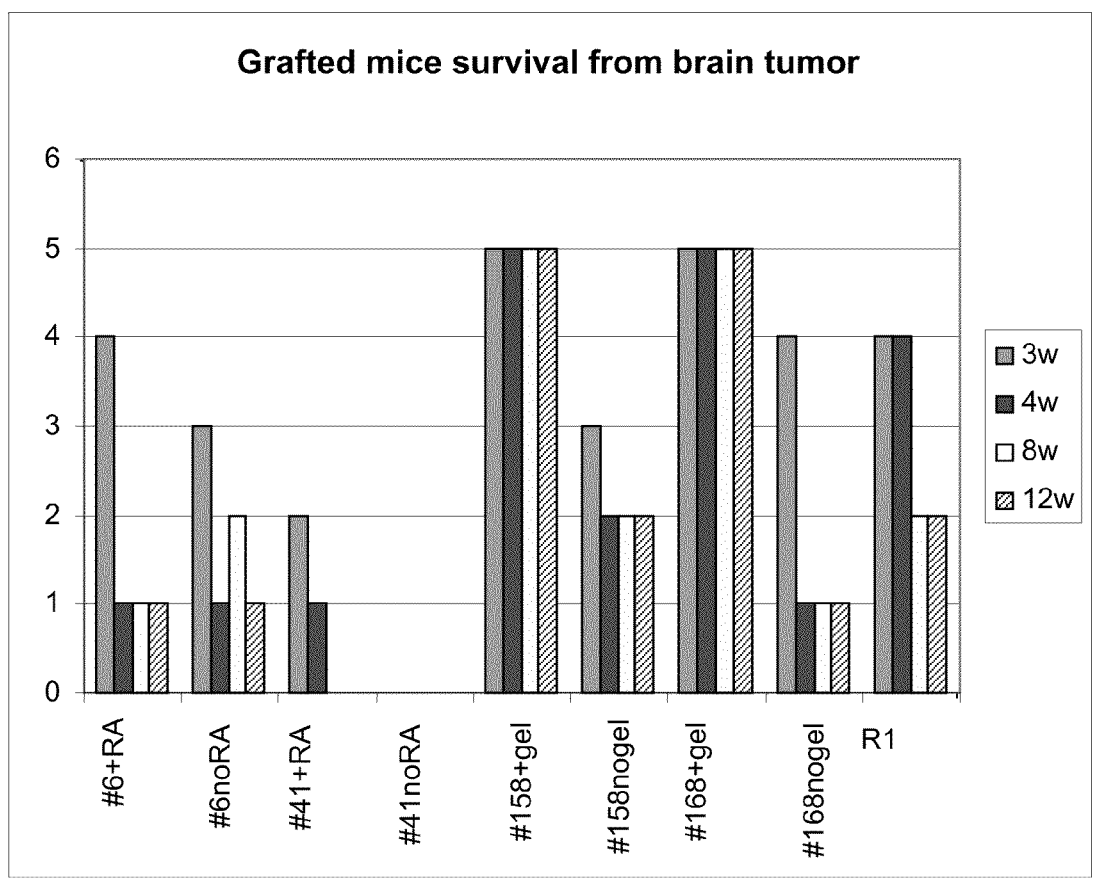

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ile Lys Val Ala Val
1               5
```

US 8,697,048 B2

PEPTIDE AMPHIPHILE SUSPENSION TO PREVENT OR REDUCE TUMOR FORMATION FROM ADMINISTERED EMBRYONIC STEM CELLS

This present application is a continuation of U.S. patent application Ser. No. 11/018,622, filed Dec. 21, 2004, which claims priority to provisional patent application Ser. No. 60/532,249, filed Dec. 23, 2003, which is herein incorporated by reference in its entirety.

FIELD OF THE INVENTION

The present invention relates to the use of self-assembling peptide amphiphiles to prevent tumor formation by transplanted stem cells. The present invention further relates to the use of self-assembling peptide amphiphiles to treat cancers.

BACKGROUND OF THE INVENTION

Embryonic stem cells are pluripotent and can give rise to virtually all cell lineages in the body. Thus there is a great clinical potential for using embryonic stem cells to replace damaged cells in any given organ or tissue. However, embryonic stem cells can be tumorigenic. Therefore, a major concern for using embryonic stem cells is tumor formation after grafting. What is needed are compositions and methods useful in preventing tumor formation after embryonic stem cell grafting.

SUMMARY OF THE INVENTION

The present invention relates to the use of self-assembling peptide amphiphiles to prevent tumor formation by transplanted stem cells. The present invention further relates to the use of self-assembling peptide amphiphiles to treat cancers.

For example, the present invention provides a method, comprising the steps of a) providing a stem cell, a peptide-amphiphile composition, and a subject; and b) administering the stem cell and the peptide-amphiphile composition to the subject (e.g., under conditions such that tumors are not formed or tumor growth or formation is reduced as compared to a subject undergoing the same treatment in the absence of the peptide-amphiphile composition). In some preferred embodiments, the stem cell comprises an embryonic stem cell or an adult stem cell. In some embodiments, the peptide-amphiphile composition comprises a hydrophobic component, a peptide or peptide-like component, and a bioactive epitope sequence. In some embodiments, the bioactive epitope sequence is IKVAV (SEQ ID NO:1). In some embodiments, the peptide-amphiphile composition is a gel. In preferred embodiments, the peptide-amphiphile composition and the stem cells are mixed prior to the administering step. While the present invention is not limited by the nature of the subject, in some embodiments, the subject is suffering from ischemia. The present invention also provides methods comprising the steps of: a) providing a peptide-amphiphile composition; and a subject, wherein the subject has a tumor; and b) contacting the peptide-amphiphile composition with the subject under conditions such that the subject's tumor is decreased in size or such that additional tumor formation or metastasis is reduced or prevented.

The present invention further provides compositions comprising one or more stem cells and a peptide-amphiphile composition. The compositions may comprise kits for research or therapeutic applications. In some embodiments, the stem cells and peptide-amphiphile composition are in contact with one another. In other embodiments, the stem cells and peptide-amphiphile composition are separate (e.g., are in separate containers in a kit).

DESCRIPTION OF THE FIGURE

FIG. 1 shows the protection of mice from tumor formation after embryonic stem cell transplantation.

DEFINITIONS

As used herein, the term "mesodermal cell line" means a cell line displaying phenotypic characteristics associated with mesodermal cells.

As used herein, the term "endodermal cell line" means a cell line displaying phenotypic characteristics normally associated with endodermal cells.

As used herein, the term "ectodermal cell line" means a cell line displaying phenotypic characteristics normally associated with ectodermal cells.

As used herein, the term "pluripotent" means the ability of a cell to differentiate into multiple different types of cells (e.g., terminally differentiated cells). For example, pluripotent cells include those that can differentiate into the three main germ layers: endoderm, ectoderm, and mesoderm.

As used herein, the terms "transplant cells" and "graft material" refer broadly to the component (e.g., tissue or cells) being grafted, implanted or transplanted. As used herein, the term "transplantation" refers to the transfer or grafting of tissues or cells from one part of a subject to another part of the same subject, or to another subject, or the introduction of biocompatible materials into or onto the body. As used herein, in some embodiments, a transplanted tissue may comprise a collection of cells of identical or similar composition, or derived from an organism (e.g., a donor), or from an in vitro culture (e.g., a tissue culture system).

The term "recipient of transplanted cells" as used herein, refers broadly to a subject undergoing transplantation and receiving transplanted cells.

As used herein, the term "cell culture" refers to any in vitro culture of cells, including but not limited to continuous cell lines (e.g., with an immortal phenotype), primary cell cultures, and finite cell lines (e.g., non-transformed cells).

The term "in vitro" refers to an artificial environment and to processes or reactions that occur within an artificial environment. The term "in vivo" refers to the natural environment (e.g., an animal or a cell) and to processes or reactions that occur within a natural environment. The definition of an in vitro versus in vivo system is particular for the system under study. As used herein, an in vitro system refers to studies of cells or processes in an artificial environment, such as in tissue culture vessels and apparatus, whereas study of the same system in an in vivo context refers to the study of cells or processes within an organism, such as a rat or human.

As used herein, the term "primary cell" or "primary culture" refers to a cell or a culture of cells that have been explanted directly from an organism, organ, or tissue. Primary cultures are typically neither transformed nor immortal.

The term "tissue culture" as used herein, refers to a collection of techniques for the growth and maintenance of cells in the laboratory. Such techniques may involve tissue culture dishes or other vessels, incubators and sterility containment devices, as known in the art.

As used herein, the term "exogenous" is used interchangeably with the term "heterologous" refer to a substance coming from some source other than its native source. For example, the terms "exogenous protein," or "exogenous cell" refer to a protein or cell from a non-native source or location, and that have been artificially supplied to a biological system. In contrast, the terms "endogenous protein," or "endogenous cell" refer to a protein or cell that are native to the biological system, species or individual.

As used herein, the term "stem cells" refers to cells that can self-renew and differentiate into multiple lineages. Stem cells may be derived, for example, from embryonic sources ("embryonic stem cells") or derived from adult sources. For example, U.S. Pat. No. 5,843,780 to Thompson describes the production of stem cell lines from human embryos. PCT publications WO 00/52145 and WO 01/00650 describe the use of cells from adult humans in a nuclear transfer procedure to produce stem cell lines.

Examples of adult stem cells include, but are not limited to, hematopoietic stem cells, neural stem cells, mesenchymal stem cells, and bone marrow stromal cells. These stem cells have demonstrated the ability to differentiate into a variety of cell types including adipocytes, chondrocytes, osteocytes, myocytes, bone marrow stromal cells, and thymic stroma (mesenchymal stem cells); hepatocytes, vascular cells, and muscle cells (hematopoietic stem cells); myocytes, hepatocytes, and glial cells (bone marrow stromal cells) and, indeed, cells from all three germ layers (adult neural stem cells).

The terms "embryonic stem cell" ("ES cell") refer to cells derived from mammalian blastocysts, which are self-renewing and have the ability to yield many or all of the cell types present in a mature animal. Human embryonic stem cell lines suitable for use with the methods and compositions of the present invention include but are not limited to those produced by the following institutions: BresaGen, Inc., Athens, Ga.; CyThera, Inc., San Diego, Calif.; ES Cell International, Melbourne, Australia; Geron Corporation, Menlo Park, Calif.; Göteborg University, Göteborg, Sweden; Karolinska Institute, Stockholm, Sweden; Maria Biotech Co. Ltd.—Maria Infertility Hospital Medical Institute, Seoul, Korea; MizMedi Hospital—Seoul National University, Seoul, Korea; National Centre for Biological Sciences/Tata Institute of Fundamental Research, Bangalore, India; Pochon CHA University, Seoul, Korea; Reliance Life Sciences, Mumbai, India; Technion University, Haifa, Israel; University of California, San Francisco, Calif.; and Wisconsin Alumni Research Foundation, Madison, Wis. The human ES cells listed on the Human Embryonic Stem Cell Registry to be created by the National Institutes of Health find use in the methods and compositions of the present invention. However, human ES cells not listed on the NIH registry are also contemplated to find use in embodiments of the present invention (e.g., when it is desirable to prevent ES contamination with nonhuman-derived materials).

As used herein the term "feeder cells" refers to cells used as a growth support in a tissue culture system. In preferred embodiments, the term "feeder cells" refers to embryonic "striatum cells," while in other embodiments the term "feeder cells" refers to stromal cells.

DETAILED DESCRIPTION OF THE INVENTION

Pluripotent stem cells such as embryonic stem cells (ESCs) can differentiate into a variety of cell types (e.g., all of the cell types) of the body and may potentially be used to repair damaged organs or tissues. However, the clinical utility of embryonic stem cells at present is very limited because they develop teratomas after transplantation into recipients. The methods of the present invention provide a novel approach involving association (e.g., co-injection) of embryonic stem cells with a self-assembling gel to prevent tumor formation by embryonic stem cells or other stem cells. Experiments conducted during the course of development of the present invention demonstrated protection against tumor formation after transplantation with the use of the gel. The present invention thus provides methods for use (e.g., research use, drug screening, therapeutic use) of embryonic stem cells for many types of disorders of different organs.

The methods of the present invention are suitable for use with a variety of stem cells including, but not limited to, embryonic stem cells and adult stem cells. Embryonic stem cells may be obtained from a variety of sources including, but not limited to, embryonic stem cell lines and embryonic germ cell lines derived from primordial germ cells (PGCS) cells isolated, according to one embodiment, from gonadal tissues, genital ridges, mesenteries or embryonic yolk sacs of human embryos (see e.g., U.S. Pat. No. 6,562,619). Embryonic stem cells may also be obtained from commercial or research sources. Adult stem cells may be derived from a variety of cell types, including, but not limited to, those disclosed above.

In some preferred embodiments, the present invention utilizes peptide-amphiphile compositions to prevent tumor formation by embryonic stem cells. Exemplary peptide-amphiphile compositions are described in WO 03/070749 and WO 03/084980; herein incorporated by reference in their entireties. In some embodiments, the composition is a gel.

The peptide-amphiphile (PA) compositions used in the present invention can be synthesized using preparatory techniques well-known to those skilled in the art—preferably, by standard solid phase chemistry, with alkylation or other modification of the N-terminus of the peptide component with a hydrophobic moiety, mono or di-alkyl moieties attached to the N- or C-termini of peptides may influence their aggregation and secondary structure in water in both synthetic and natural systems. A hydrophobic, hydrocarbon and/or alkyl tail component with a sufficient number of carbon atoms coupled to an ionic peptide having a preference for beta-strand conformations can in certain embodiments be used to create an amphiphile that assembles in water into nanofiber structures. The amphiphile's overall conical shape can also have an effect on such assemblies. Self-assembling can also be triggered by body fluid (e.g., cerebral spinal fluid).

In some embodiments, the peptide amphiphile compound/composition has 1) a hydrophobic component and 2) a peptide or peptide-like component further including a bioactive epitope sequence. In various preferred embodiments, the hydrophobic component of such a compound or composition is of sufficient length to provide amphiphilic behavior and nanofiber assembly/formation in water or another polar solvent system. Typically, such a component may be about a C6 or greater hydrocarbon moiety, although other hydrophobic, hydrocarbon and/or alkyl components could be used as would be well-known to those skilled in the art to provide similar structural or functional effect. Such hydrophobic components include, without limitation, cholesterol, biphenyl and p-aminobenzoic acid.

In some embodiments, the bioactive epitope is an IKVAV (SEQ ID NO:1) sequence. IKVAV (SEQ ID NO:1) is a laminin sequence known to interact with mammalian neurons. IKVAV (SEQ ID NO:1) promotes neurite outgrowth in mammalian neurons. The present invention is not limited to the use of IKVAV (SEQ ID NO:1). Other suitable bioactive epitopes find use in the methods of the present invention.

Peptide components of this invention preferably comprise naturally-occurring amino acids. However, incorporation of known artificial amino acids such as beta or gamma amino acids and those containing non-natural side chains, and/or other similar monomers such as hydroxyacids are also contemplated, with the effect that the corresponding component is peptide-like in this respect.

In some embodiments, the PA compositions form a sol-gel system including 1) a polar or aqueous solution and/or containing of one or more of the amphiphile compounds or compositions described herein, and 2) a factor or reagent sufficient to induce assembly, agglomeration of gelation under neutral or physiological conditions. Such gelation and/or self-assembly of various PA compositions into micellular nanofibers can be achieved under substantially neutral and/or physiological pH conditions through drying, introduction of a mono- or multivalent metal ion and/or the combination of differently charged amphiphiles.

Experiments conducted during the course of development of the present invention demonstrated that transplantation of embryonic stem cells improves functional outcome after brain ischemia in rats. However, about 20~30% of the recipients died of brain tumors. In contrast, when the peptide amphiphiles was co-injected with the embryonic stem cells, the animals did not develop tumors. Accordingly, in some embodiments, the present invention provides methods of preventing tumor formation upon introduction of stem cells (e.g., embryonic stem cells or ESCs) into a subject. In some embodiments, the gels are co-injected during ESC transplantation in any organ to prevent teratoma formation. In some embodiments, the gels and the stem cells are mixed prior to injection. Any suitable stem cell or peptide-amphiphile composition may be utilized. Preferred compositions are non-toxic. A variety of stem cells may be utilized, depending on the application.

In other embodiments, the peptide-amphiphile compositions are used for cancer treatment in situ. For example, in some embodiments, peptide amphiphile (e.g., those described herein) are injected directly at the site of a tumor or cancer. The treatment may be repeated as needed until the tumor is reduced in size or eliminated.

EXPERIMENTAL

The following examples are provided in order to demonstrate and further illustrate certain preferred embodiments and aspects of the present invention and are not to be construed as limiting the scope thereof.

Example 1

Protection of ESC-Transplanted Mice Against Tumor Formation

This Example describes the protection of embryonic stem cell (ESC) transplanted mice against tumor formation in the presence of peptide amphiphiles (IKVAV-peptide amphiphile).

A. Methods

Animal Model of Focal Brain Ischemia

Under anesthesia (Avertin, 0.2 ml/10 gram body weight, i.p.), an incision was made between left ear and eye in adult female mice (129sv, 4-8 w). A craniotomy was performed, and the middle cerebral artery was exposed. Thereafter, the left middle cerebral artery was cauterized, and the incision was sutured by a 3-0 silk surgery suture.

Embryonic Stem Cell Preparation

Embryonic stem cells (R1, a cell line derived from 129sv mice) were propagated in DMEM defined medium (20% fetal bovine serum, 0.1 mM of non-essential amino acids, 50 µg/ml of penicillin-streptomycin, 0.1 mM of L-glutamine, 1000 U/ml of leukemia inhibitory factor, 100 µM of β-mercaptoethanol). The cells were harvested with 0.05% trypsin-EDTA. After washing with HBSS (Hanks' Balanced Salt Solution) twice, the cells were then re-suspended in IKVAV-PA or glucose (vehicle for IKVAV-PA). The cell concentration was prepared as 50~100,000 cells/µl.

Transplantation

One week after brain ischemia, the mice were anesthetized with Avertin. The animals were fixed in a KOPF brain frame, and 2 µl of embryonic stem cells were stereotoxically injected into the left cortex surrounding the infarction by using a 10-µl Hamilton microsyringe. Two sites were selected for grafting: 1) 0.26 mm rostal to the bregma, 2.5 mm lateral to the midline, 1.5 mm ventral to the dura; 2) 2.06 mm caudal to the bregma, 2.5 mm lateral to the midline, 1.5 mm ventral to the dura. The tooth bar was set at −2. The cells were injected through 2 minutes and the cannula was kept in situ for 5 minutes before removal.

Tumor Formation

After grafting, the mice were monitored every week. Dead animals with large brain tumors were removed out from their cage.

B. Results

ESCs were suspended with the self-assembling IKVAV-peptide amphiphile (gel) or with vehicle before grafting. Female adult 129SV mice were subjected to permanent middle cerebral artery occlusion to induce brain ischemia. One week after brain ischemia, the mice were randomly divided into nine groups (5 mice/group). Two microliters of ESC suspension (50~100,000 cells/0, 2 sites/brain) were stereotaxically injected into the cortex surrounding the infarctions. The results are shown in FIG. 1. R1 is the wild type strain of mouse for the embryonic stem cells used in these experiments. #6, #41, #158 and #168 are clones of SOX1 promoter-eGFP engineered R1 ESCs. RA (retinoic acid) has been reported to induce embryonic stem cell differentiation into neural cells. As early as three weeks after ESC transplantation, the animals without the gel started dying from tumors. All of the mice that received #41 ESCs without RA treatment died at 3 weeks after grafting. Three months after transplantation, 60%~80% of ESC grafted mice died of brain tumor. In contrast, the mice that grafted with ESC+IKVAV-PA all survived at 3 months after grafting.

ESCs were also found to survive after seeding in vitro with IKVAV-PA. ESCs were seeded with IKVAV-AP ($4 \times 10^4$ cells/ml) and they survived well 2 days after seeding. ESC viability was assayed 7 days after seeding with IKVAV-PA or seeding on PDL coated cover slips using fluorescence microscopy. These data indicated that IKVAV-PA was not cytotoxic to embryonic stem cells. In other words, IKVAV-PA did not kill the embryonic stem cells before and after transplantation. ESCs were shown using fluorescence microscopy to differentiate into neuronal like cells 3 weeks after seeding in IKVAV-PA.

Example 2

Transplantation of Glioma Cells (9L) with Self-Assembling Gel under the Skin This example describes the use of peptide-amphiphile gels to inhibit tumor formation in vivo.

Preparation of Glioma Cells in Vitro

Gliosarcoma (9L) cells, derived from Fischer 344 rats, are grown in DMEM medium with 10% fetal bovine serum, and are collected with 0.05% trypsin-EDTA. The cells are washed with HBSS twice and $10^7$ cells are re-suspended with 300 μl IKVAV-PA or glucose (vehicle control) or HBSS.

Transplantation of Glioma Cells with Self-Assembling Gel

Tumor cells are suspended with IKVAI-PA or glucose. The cells are then injected subcutaneously in the shaved left flanks of anesthetized rat (female Fischer 344, 100~150 g. Measurement of tumor formation is performed weekly.

Transplantation of Glioma Cells Followed by Self-Assembling Treatment

Glioma cells are re-suspended with HBSS at a concentration of $10^7$ cells/300 μl, and are then injected into the shaved right flanks of Fischer 344 rats under anesthesia. Three weeks after grafting, the rats are randomly divided into two groups. One group of the grafted rats receives IKVAV-PA injection (5 sites: 4 in the periphery and one in the central of the tumor; 50 μl/site). In the control group, the same volume of glucose is injected into the tumor. The peptide or glucose is given twice a week. Tumor size is measured once a week.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method preventing or reducing tumor formation by transplanted embryonic stem cells, comprising administering to the brain of a subject:

(a) a micellular nanofiber structure suspension comprising:
      (i) an embryonic stem cell; and
      (ii) a peptide amphiphile comprising:

(A) a hydrophobic component of sufficient length to provide amphiphilic behavior and micellular nanofiber assembly in water, and
         (B) a peptide component comprising a bioactive epitope sequence,
      wherein said bioactive epitope sequence is an IKVAV sequence; and
   (b) retinoic acid,
   wherein tumor formation in the brain of the subject is prevented or reduced.

2. The method of claim 1, wherein said peptide-amphiphile is a gel.

3. The method of claim 1, wherein said subject is suffering from ischemia.

* * * * *